United States Patent [19]

Richter et al.

[11] Patent Number: 5,882,544
[45] Date of Patent: Mar. 16, 1999

[54] POLYCYCLIC IMINOOXADIAZINEDIONES FROM (CYCLO)ALIPHATIC 1,4-DIISOCYANATES

[75] Inventors: Frank Richter; Dieter Mager, both of Leverkusen; Josef Pedain, Köln, all of Germany

[73] Assignee: Bayer Aktiengesellschaft, Leverkusen, Germany

[21] Appl. No.: 989,066

[22] Filed: Dec. 11, 1997

[30] Foreign Application Priority Data

Dec. 20, 1996 [DE] Germany .................. 196 53 583.2

[51] Int. Cl.$^6$ .................. C09K 3/12; C07D 273/04; C07D 267/14; A61K 31/535
[52] U.S. Cl. .................. 252/183.12; 544/67; 544/68; 540/545; 540/552; 514/229.2; 252/183.12
[58] Field of Search .................. 540/545, 552; 544/67, 68; 514/229.2; 594/68; 252/183.12

[56] References Cited

U.S. PATENT DOCUMENTS

| | | | |
|---|---|---|---|
| 4,912,210 | 3/1990 | Disteldorf et al. | 540/202 |
| 5,013,838 | 5/1991 | Scholl | 544/193 |
| 5,717,091 | 2/1998 | Richter et al. | 544/67 |

FOREIGN PATENT DOCUMENTS

| | | |
|---|---|---|
| 571038 | 11/1993 | European Pat. Off. . |
| 19611849 | 10/1997 | Germany . |

OTHER PUBLICATIONS

B. Akteries et al, Chemische Berichte, vol. 119, 1986, pp. 1133–1143, XP002059955.
R. J. Cotter & M. Matzner "Organic Chemistry, A Series of Monographs", Part 2, vol. 13B2, p. 332 ff. cf. also Example 1.
Chem. Ber., 60, (1927), 295 and 1011.
C.R. Acad. Sci. Ser. C 277 (1973) 795.
Chem. Ber. 120 (1987), 339.

*Primary Examiner*—Johann Richter
*Assistant Examiner*—Dominic Keating
*Attorney, Agent, or Firm*—Joseph C. Gil; Thomas W. Roy; Diderico van Eyl

[57] ABSTRACT

The present invention relates to polycyclic iminooxadiazinediones A corresponding to formula I

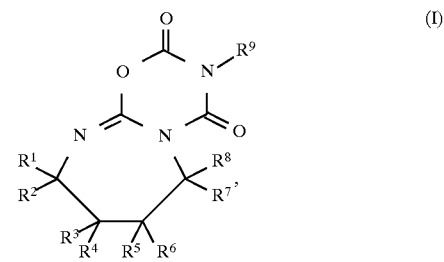

The present invention also relates to mixtures of these polycyclic iminooxadiazinediones with other isocyanate derivatives and to their use for the production of optionally foamed polyurethane plastics, for the production of paints and coatings and for the production or formulation of active ingredients, pharmaceutical products, etc.

6 Claims, No Drawings

POLYCYCLIC IMINOOXADIAZINEDIONES FROM (CYCLO)ALIPHATIC 1,4-DIISOCYANATES

BACKGROUND OF THE INVENTION

1. Field of the Invention

The present invention relates to polycyclic iminooxadiazinediones prepared from 1,4-diisocyanates, to a process for their production and to their use for the production of polyisocyanate addition products.

2. Description of the Prior Art

The reaction of isocyanates with an exceptionally large number of H-acid compounds to synthesize high molecular weight polymers based on the work of O. Bayer et al. is known (for example, DE-A 728,981) and has found substantial industrial application. Use is made of the high reactivity of the isocyanate groups with the co-reactants.

The unpleasant physiological properties of low-molecular isocyanates, in particular diisocyanates, occasionally prevent their direct use, for example, in the coatings sector. Various methods are therefore employed for the modification of these monomers with the aim of considerably increasing the vapor pressure of the resulting products and obtaining physiologically safe compounds. Examples of this are the reaction of excess quantities of diisocyanates with dihydric and polyhydric alcohols to form prepolymers as well as the preparation of polyisocyanates saving uretdione ("dimer"), isocyanurate ("trimer") and biuret groups.

In addition, it is occasionally necessary to use NCO groups having reduced reactivity, e.g., in one-component applications with as long a pot life as possible, polyurethane powder coating systems and aqueous systems. To obtain products which can be employed in these applications, it is necessary to carry out a thermally or chemically reversible blocking reaction using compounds, which are split off, optionally in altered form, during the cross-linking reaction to form the polymeric synthetic material or coating film (for example, Progr. Org. Coatings, 3 (1975), 73 and 9 (1981), 3). A number of compounds have proven to be successful in practice for this purpose, for example, ∈-caprolactam, dialkyl malonate esters and butanone oxime.

The disadvantage of all these systems is that the blocking agents, which are split off during the curing reaction, have to be disposed of. Otherwise, if they remain in the products, they can adversely affect their range of properties, for example, due to "exudation" or to a deterioration in the physical and/or chemical stability of the products.

In some respects an exception to this disadvantage are the above-mentioned coating polyisocyanates containing uretdione groups ("dimers"), which, in contrast to the many other isocyanate derivatives, may be thermally split into the original isocyanates. Therefore, no decomposition product is released during the curing process.

However, several disadvantages may result from the thermal lability of the uretdione structure. Prolonged storage at an elevated temperature may lead to a slow splitting of the uretdione rings, which results in an increase in the content of residual monomers and consequently in products which are no longer physiologically unobjectionable. Also, the thermally induced dissociation of the uretdione rings, which is necessary for the rapid curing of the composition, takes place only at relatively elevated temperatures, which may lead to discoloration and other unwanted decomposition phenomena.

Also known is the use of the "self-blocking" compounds of the so-called α-nylon type, which are described in EP-A 14,365 and are similar to uretdiones. However, the splitting of these polymers, which is necessary for the cross-linking, succeeds if at all only at higher temperatures than the temperatures needed for uretdiones. For this reason they have not been previously used, in particular in the coatings sector.

An object of the present invention is to develop systems wherein none or at least a distinctly decreased amount of the isocyanate groups, when compared to known prior art systems containing blocking agents, have to be deactivated by the addition of a blocking agent and nevertheless, even at elevated temperature, do not split into monomeric diisocyanates.

This object may be achieved with the bicyclic and polycyclic iminooxadiazinediones (hereinafter polycyclic iminooxadiazinediones) according to the invention.

SUMMARY OF THE INVENTION

The present invention relates to polycyclic iminooxadiazinediones A corresponding to formula I

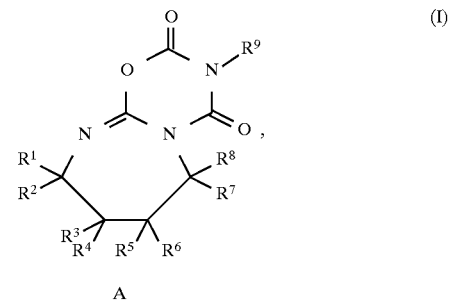

wherein $R^1$ to $R^8$ are identical or different and represent hydrogen or alkyl, cycloalkyl, aralkyl and aryl groups, which may be substituted isocyanato(cyclo)alkyl groups or by groups which are not reactive with isocyanate groups, or $R^1$ and/or $R^2$ can form one or more, optionally partially unsaturated rings, with one another and also with one or more substituents from among $R^3$ to $R^4$ and the corresponding carbon atoms of the seven-membered ring segment in A, or $R^3$ or $R^4$ can form an aromatic ring with $R^5$ or $R^6$ and with the two carbon atoms of the seven-membered ring segment in A which are not bonded to nitrogen, and $R^9$ represents hydrogen or an alkyl, cycloalkyl, aralkyl, aryl, or heterocyclic group which may be substituted by isocyanato(cyclo)-alkyl groups or by groups which are not reactive with isocyanate groups.

The present invention also relates to mixtures of these polycyclic iminooxadiazinediones with other isocyanate derivatives containing isocyanurate, uretdione, biuret, allophanate, carbodiimide and/or urethane group and optionally isocyanate groups, wherein the isocyanate groups may optionally be present in blocked form.

The present invention further relates to a process for the preparation of these polycyclic iminooxadiazinediones by the catalytically induced reaction of a diisocyanate or isocyanate group-containing oligomer C corresponding to formula (III)

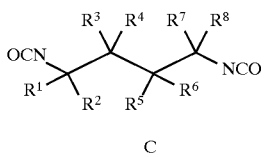

C with at least one identical or different mono- or polyisocyanate.

Finally, the present invention relates to the use of the polycyclic iminooxadiazinediones according to the invention as an intermediate product and as a component for the production of optionally foamed polyurethane plastics, for the production of paints and coatings and for the production or formulation of active ingredients, pharmaceutical products, etc.

DETAILED DESCRIPTION OF THE INVENTION

In accordance with formula I, $R^9$ may represent a group corresponding to formula

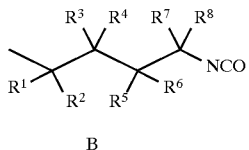

B wherein $R^1$ to $R^8$ are as previously defined.

Also in accordance with the preceding formulas, examples of groups that do not react with isocyanate groups include halogen, oxo (—C(=O)—), alkoxy or aryloxy (R—O—), alkoxycarbonyl (ROC(=O)—), aroyl (RC(=O)—) a.s.o. may be present in or as substituents $R^1$–$R^9$.

The present invention is based on the surprising observation that 1,4-diisocyanates, optionally in the presence of other mono- and/or polyisocyanates, can be converted by a catalytically induced reaction into the polycyclic iminooxadiazinediones according to the invention. This finding is very surprising, because it is known from the literature that 1,4-diisocyanates, over a wide temperature range and in the presence of different catalysts, either tend to oligomerize (trimerization with the formation of isocyanurate groups, cf. for example EP 571,038, or dimerization with the formation of uretdione groups) or, often simultaneously, tend to (cyclo) -polymerization with the formation of high molecular weight compounds of the α-nylon type. This is described, with further literature references, in R. J. Cotter and M. Matzner "Organic Chemistry, A Series of Monographs", Part 2, Vol. 13B2, pages 332 ff., and also in Example 1. As previously mentioned above, the latter α-nylon type species have serious disadvantages with regard to their use e.g. in coating applications. The preceding references did not mention the formation of polycyclic iminooxadiazinediones.

There are only a few citations in the literature in which the formation of iminooxadiazinedione compounds by the catalytically induced modification of isocyanates is described. Slotta and Tschesche obtained the monocyclic trimethyl derivative (3,5-dimethyl-2-methylimino-4,6-diketo-1,3,5-oxadiazine), in addition to other products, during the conversion of methyl isocyanate in the presence of tributylphosphine (Chem. Ber., 60, (1927), 295 and 1011). This compound is said to be obtainable in better yield if the reaction is carried out in 1,2-dichloro-ethane as solvent (C. R. Acad. Sci. Ser. C 277 (1973) 795). 3-phenyl-5-methyl-2-methylimino-4,6-diketo-1,3,5-oxadiazine, which is theoretically prepared from one equivalent of phenyl isocyanate and two equivalents of methyl isocyanate, is formed together with other products in the reaction of diphenyl methyl-imidocarbonate with tosyl isocyanate (Chem. Ber. 120 (1987), 339). The formation of a minor amount of the tris(6-isocyanatohexyl) derivative, i.e., 3,5-bis (6-isocyanatohexyl)-2-(6-isocyanatohexyl)imino-4,6-diketo-1,3,5-oxadiazine during the trimerization of hexamethylene diisocyanate in the presence of carbon dioxide is mentioned in DE-A 3,902,078. These compounds can be specifically prepared from the information in DE-A 19,611, 849.

Polycyclic compounds having the iminooxadiazinedione structure were recently still completely unknown. Representatives which are obtainable starting from 1,3-diisocyanates are described in DE-A 19,532,060.

The polycyclic iminooxadiazinediones according to the invention can be prepared by the catalytically induced reaction of polyisocyanates, preferably diisocyanates, optionally in combination with other mono- or polyisocyanates as coreactants, wherein in at least one of the starting components two of the isocyanate groups are arranged in the 1,4 positions to one another.

The 1,4-diisocyanates to be used for the preparation of the polycyclic iminooxadiazinediones according to the invention are compounds having a number average molecular weight of 140 to 800, preferably 140 to 400. These diisocyanates may optionally be used in admixture with other mono- and polyisocyanates and, where possible, may optionally be used in the form of mixtures of stereoisomers. Examples of 1,4-diisocyanates include 1,4-diisocyanatobutane (butane diisocyanate or BDI), 2,2,3,3-tetrafluoro-1,4-butane diisocyanate, 2-chloro-1,4-diisocyanatobutane, 2,3-dibromo-1,4-diisocyanatobutane, 2,3 -bis (di-fluoroamino)-1,4-diisocyanatobutane, 1,4-diisocyanato-1,1,2,2,3,3,4,4-octafluoro-butane, 1,4-diisocyanato-l-propoxybutane, 1,4-diisocyanatopentane, 1,4-diisocyanato-4-methyl-pentane, 2,5-diisocyanatohexane, 3,6-diisocyanatooctane, 1-isocyanato-3-(isocyanatomethyl)pentane, 2,5-diisocyanato-2,5-dimethylhexane, 1-isocyanato-3-(isocyanatomethyl)-3,5,5-trimethylhexane, 1,3,6-triisocyanatohexane, 2,5,8-triisocyanatooctane, 1,4-diisocyanato-1-butene, 1,4-diisocyanato-2-butene, 2-butanedioyl diisocyanate, 2-butenedioyl diisocyanate, 4,7-diisocyanato-2,6,6-trimethyl-2-heptene, 1-methylene-1,4-butane diisocyanate, ethyl, propyl, benzyl, butyl, hexyl, octyl, decyl, dodecyl and octadecyl esters of 2,5-diisocyanatopentanoic acid, methyl 2,5-diisocyanatohexanoate, methyl 2,5-diisocyanatoheptanoate, dimethyl, diethyl and dibutyl esters of 2,5-diisocyanato-dihexanoic acid, 1,2 bis(iso cyanatomethyl)cyclobutane, 1,4-diisocyanatocyclohexane, 1,4-diisocyanato-2-methylcyclohexane, 1,2-bis (isocyanatomethyl)cyclohexane, 5,6-bis-(isocyanatomethyl) bicyclo-[2.2.1]hept-2-ene, 1,4-diisocyanato-bicyclo[2.2.2]-octane, 2-isocyanato-6-isocyanatomethylpyran, 1,1-dimethyl-3-isocyanato-5-isocyanatomethyl-cyclohexane, 2-isocyanato-4-isocyanatomethyl-1,1,4-trimethylcyclohexane, 2-isocyanato-4-isocyanatomethyl-1, 1-dimethylcyclobutane, 1,4-diisocyanato-2,3,5,6-tetramethylcyclohexane, 1-isocyanato-3-isocyanatomethyl-1-methylcyclohexane (optionally also in a mixture with the two isomers of 1-isocyanato-4-isocyanatomethyl-1-methylcyclohexane, IMCI), 2-isocyanato-4-isocyanatomethyl-1-methylcyclohexane, 5-isocyanato-1-isocyanatomethyl-1,3,3 -trimethylcyclohexane (IPDI), 2,5-diisocyanato-1,1,3-trimethylcyclohexane, 1-isocyanato-3-isocyanato-methylcyclohexane, 1-isocyanato-3-(1-isocyanatoethyl)cyclohexane, 1-isocyanato-3-(1- isocyanatopropyl)cyclohexane, 4-cyclohexene-1,2-dicarbonyl diisocyanate, 1,2-bis(isocyanatomethyl)benzene (xylylene diisocyanate, XDI), 1,2-bis(1-isocyanato-1-methylethyl)benzene (tetramethylxylylene diisocyanate or TMXDI), 4,5-bis(isocyanatomethyl)-1,3-dithiolane, 4,5-bis(isocyanatomethyl)-2-methyl-1,3-dithiolane, 2-(2-isocyanatoethyl)-2-(isocyanatomethyl)-1,3-dithiolane, 2-(2-isocyanato-ethyl)-2-(isocyanatomethyl)-1,3-dioxolane, 3,4-bis(isocyanatomethyl)tetra-hydrothiophene, 2,3-bis(isocyanatomethyl)-1,4-dithiane, 1,2,3,4-tetramethoxy-1,4-butane diisocyanate and 1,4-diisocyanato-1,2,3,4-butanetetrol tetraacetate.

These 1,4-diisocyanates are known and can be prepared by established prior art processes, with or without the use of phosgene, for example, from the corresponding diamines or by other routes (Curtius decomposition, urethane splitting, etc).

When cycloaliphatic 1,4-diisocyanates are used and, in particular, when mixtures of stereoisomers having a high proportion of 1,4-cis isomers or a high proportion of 1,3-trans isomers are used, other modification reactions are possible. These include trimerization with the formation of isocyanurate structures as well as monocyclic iminooxadiazinedione structures (cf. DE-A 19,611,849), and carbodiimide/uretonimine formation as well as dimerization with the formation of uretdione structures. Consequently, the polycyclic iminooxadiazinediones according to the invention can also arise in admixture with previously mentioned isocyanate derivatives from prior art such as ureas, biurets, urethanes and/or allophanates, or may be mixed with them afterwards. The polycyclic iminooxadiazinediones according to the invention may also be formed along with (cyclo)polymerizates (α-nylon compounds), from which they may optionally be separated, for example, by extraction or distillation.

The polycyclic iminooxadiazinediones according to the invention can also be obtained in pure form by starting from 1,4-diisocyanates and, in particular in the case of the cycloaliphatic diisocyanates, from pure trans-1,4-diisocyanatocycloalkanes or from pure cis-1-isocyanato-3-(1-isocyanatoalkyl) derivatives and by purifying the products or mixtures of products formed by one or more known prior art methods such as distillation, film distillation, molecular distillation, crystallization or extraction.

Many of the compounds cited in the literature for the preparation of oligomers containing isocyanate groups and also isocyanurate, monocyclic iminooxadiazinedione and/or uretdione groups are suitable for the preparation of the polycyclic iminooxadiazinediones A according to the invention. It is preferable, in particular when the preparation is carried out at temperatures below about 120° C., to use soft Lewis bases such as alkylphosphines, for example, tributylphosphine or trioctylphosphine (each optionally as mixtures of isomers) and dialkylamino-pyridines such as, for example, 4-(N,N-dimethylamino)pyridine (DMAP). The catalysts may be used in free form (homogeneous catalysis, cf. H. J. Laas et al., J. Prakt. Chem. 336 (1994, 192–198) or in chemically modified form, fixed on supports (heterogeneous catalysis, cf. EP 0,447,516 A1 or WO 93/18014). Other additives, for example, those which improve the color index of the resulting products may also be used (cf., for example, EP-A 735,027).

The suitability of these catalysts for the preparation of isocyanate derivatives containing isocyanurate and/or uretdione groups is known (cf. DE-A 1,670,720 and DE-A 3,379,549). However, their use for the preparation of the polycyclic iminooxadiazinediones according to the invention has not been mentioned. In DE-A 1,670,720 mention is made of the possibility of forming "alkyliminodialkyl-oxadiazinediones" in addition to carbodiimides and uretonimines under certain reaction conditions, e.g, elevated temperature and low concentration of catalyst. However, these assertions are only partly correct, cf. the reasoning in DE-A 19,611,849 and the comparison examples presented there. Nowhere in the literature is there a reference to the bi- or polycyclic iminooxadiazinediones according to the invention, nor to the special benefits obtained by using 1,3-diisocyanates (cf. DE-A 19,532,060) and to 1,4-diisocyanates (the present invention) in their formation.

DE-A 3,739,549 discloses the use of (cyclo)aliphatic diisocyanates having 6 to 15 carbon atoms, which in the presence of 4-dialkylamino-pyridines (for example, DMAP), can be converted with 99% selectivity into polyisocyanates having a pure uretdione structure. The simplest representative of the polycyclic iminooxadiazinediones described in the present invention, 10-(4-isocyanatobutyl)-8-oxa-1,6,10-triazabicyclo[5.4.0$^{17}$]undec-6-en-9,11-dione D, formed from two molecules of 1,4-butane diisocyanate (BDI) and corresponding to formula IV

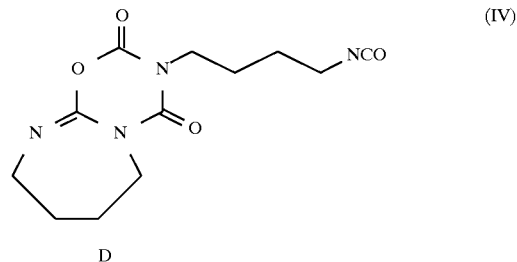

D would not fall within the description of DE-A 3,739,549.

Accordingly, from the information in the literature it could not be predicted that the above catalysts or other catalysts would be suitable for the formation of the polycyclic iminooxadiazinediones according to the invention, either alone or in admixture with other isocyanate derivatives.

The reaction can be carried out employing neat di- or polyisocyanate(s) as (a) starting material(s), optionally in the presence of a solvent which is inert to isocyanate groups, optionally at a pressure other than ambient pressure, and at a temperature of 0° C. to the decomposition temperature of the starting (di)isocyanate. The polycyclic iminooxadiazinediones according to the invention are preferably prepared at a temperature of −30° C. to 550° C., preferably from 0–500° C.

At the desired degree of conversion of the starting compound(s), the reaction can be terminated in known manner (J. Prakt. Chem. 336 (1994), 192–198), for example, by addition of a catalyst poison and/or by thermal deactivation of the catalyst. However, the reaction may also be carried out to substantially complete conversion of the monomeric 1,4-diisocyanatoalkanes. The products thus obtained may be used directly in the applications further described below. Otherwise, the product can subsequently be separated from remaining unreacted monomers in known manner, e.g., by distillation, film distillation or extraction.

In one particular, optionally continuous, embodiment of the process, the reaction can be carried out in a tubular reactor optionally with the aid of a diluent which is inert to the reaction components. The temperatures of the reaction medium are preferably from 50° C. to 550° C.

The polycyclic iminooxadiazinediones according to the invention may also be prepared by a suitable contact in the gas phase. The optimal reaction temperatures for this embodiment of the process depend upon the boiling point(s) of the starting isocyanate (mixture) and are from 100° C. to 500° C. The pressure is preferably from 1 mbar to 5 bar.

The polycyclic iminooxadiazinediones according to the invention, optionally in a mixture with other known isocyanate derivatives, can be isolated by conventional prior art methods such as thin film distillation, extraction, crystallization or molecular distillation, and are obtained as colorless or lightly colored liquids or solids. The latter have a melting range of approximately 30° C. to 190° C., depending on the (mixtures of) isocyanates used.

The polycyclic iminooxadiazinediones according to the invention are extremely valuable raw materials, which are suitable both as intermediate products for the preparation or formulation of active substances and for use in the plastics and coatings sector.

The representative substances which are obtainable from optionally branched, open-chain aliphatic 1,4-diisocyanates (bicyclic iminooxadiazinediones, for example, D, cf. also Examples 2 to 4) are low viscosity liquids, which in addition to the advantages already discussed are also eminently suitable as so-called reactive diluents for use in high solids polyurethane coatings. It is an advantage that a portion of the isocyanate groups are present in the iminooxadiazinedione ring in self-blocked form such that the reaction with the coreactant necessary for molecular weight buildup is made accessible only under suitable reaction conditions, for example, by raising the temperature and/or by the use of catalysts (cf. Examples 6 to 8).

The polycyclic iminooxadiazinediones according to the invention may be used by themselves or in combination with other known polyisocyanate derivatives, i.e., those containing uretdione, biuret, allophanate, isocyanurate, urethane and carbodiimide groups, and whose free NCO groups have optionally been blocked with known blocking agents. In this connection it is irrelevant whether the polycyclic iminooxadiazinediones according to the invention are formed during the preparation of these polyisocyanate derivatives or whether they are mixed with them afterwards.

Preferably, mixtures of polycyclic iminooxadiazinediones with polyisocyanates containing uretdione, isocyanurate and/or monocyclic iminooxadiazinedione (asymmetric trimers) groups are used. These polyisocyanate mixtures may optionally contain free NCO groups or blocked isocyanate groups. The content of polycyclic iminooxadiazinedione in the mixture is preferably not less than 10 mole % (cf. also Examples 2 to 4).

An advantage of the polycyclic iminooxadiazinediones according to the invention is that they do not exhibit any tendency to splitting into the starting monomeric (di) isocyanates during prolonged thermal stress (cf. also Example 5). Also, they possess a sufficiently high, optionally graduated reactivity towards compounds containing isocyanate-reactive groups, i.e., Zerewitinoff-active hydrogens. These observations are surprising in that it is known from the study of isomeric isocyanurates that this heterocyclic ring system is extremely inactive chemically. In addition, in the literature there is only one indication that the iminooxadiazinedione ring can be subjected to a solvolysis reaction (Chem. Ber., 60 (1927), 295).

If there are other reactive centres, for example, isocyanate groups, among or in the substituents $R^1$ to $R^9$ of formula I, the polycyclic iminooxadiazinediones according to the invention present themselves for applications with a dual cross-linking mechanism. For example, the free reactive group(s), for instance, isocyanate groups, are reacted in an initial reaction step with a component $Z(OH)_n$ or $Z[N(R')H]_n$ (cf. Scheme 1) and then cross-linking accompanied by decomposition of the iminooxadiazinedione structure is carried out in an independent, optionally catalyzed, second step. Up to two coreactants containing Zerewitinoff-active hydrogen can be bonded per equivalent of iminooxadiazinedione unit (Scheme 1).

Scheme 1:

chain-extending and cross-linking reactions with the polycyclic iminooxadiazinediones according to the invention, shown here by the example of the reaction of the simplest representative D.

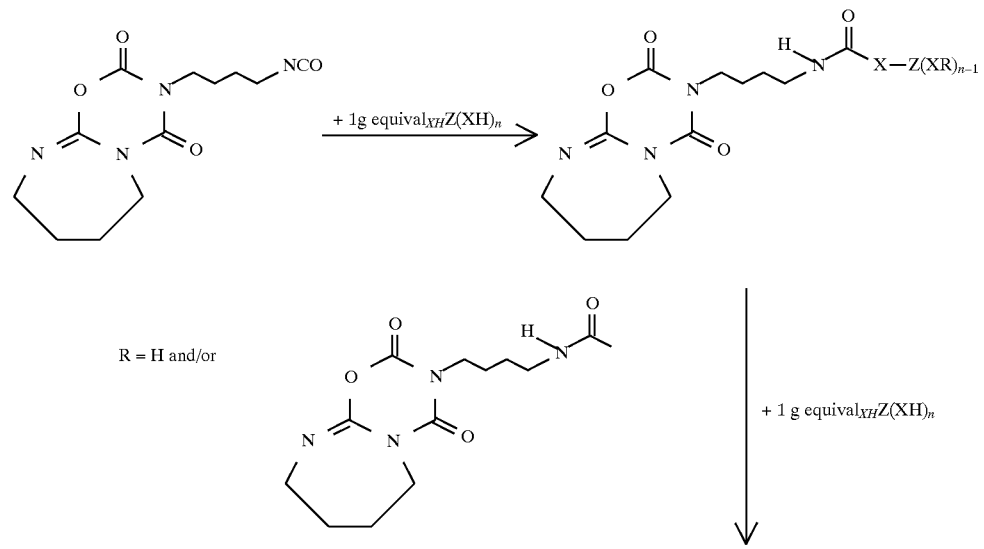

-continued
Scheme 1:
chain-extending and cross-linking reactions with the polycyclic iminooxadiazinediones according to the invention, shown here by the example of the reaction of the simplest representative D.

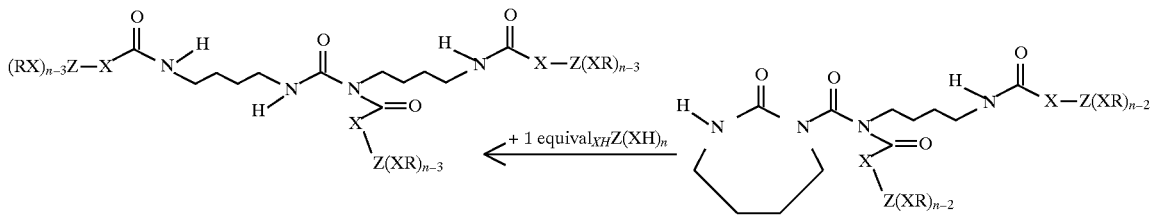

Z represents hydrogen, an n-valent alkyl, cycloalkyl, aralkyl or aryl group, or the residue obtained by removing the OH— and/or N(R')H groups from an n-valent polyacrylate, polyester, polycarbonate or polyether containing one or more amino or hydroxyl groups, X represents O or NR', R' represents hydrogen, a monovalent alkyl, cycloalkyl, aralkyl or aryl group, or the residue obtained by removing the OH— and/or N(R')H group from a monovalent polyacrylate, polyester, polycarbonate or polyether containing one amino or hydroxyl group, and n is 1 to 6.

When Z represents hydrogen the group $Z(XH)_n$ corresponds to $H_2O$, $NH_3$ or $N_2H_4$.

In principle, any required functionality can be obtained by the simultaneous presence of other reactive centers in the molecule of the polycyclic iminooxadiazinediones according to the invention or by an appropriate modification in the above-mentioned "pre-extension step" in the presence of a more than monofunctional component $Z(XH)_n$ (n>1). The products obtained in the first reaction step can also be used as one-component compositions, in which cross-linking (curing) to obtain the final product is carried out by the thermally and/or catalytically induced decomposition of the iminooxadiazinedione structure. Such products are suitable, for example, as one-component polyurethane powder coating compositions.

Curing to form the final product may also take place in a single step (two-component technology). The resulting products, regardless of whether they have been produced by a one-component or two-component route, exhibit the high quality of known polyurethane systems.

In addition to the products according to the invention and the optional coreactants, the compositions may also contain solvents or mixtures of solvents such as toluene, xylene, cyclohexane, chlorobenzene, butyl acetate, ethyl acetate, ethylene glycol acetate, methoxypropyl acetate, acetone, petroleum spirits, higher substituted aromatics (e.g., Solvent Naphtha, Solvesso, Shellsol, Isopar, Nappar and Diasol solvents). Also suitable are additives such as wetting agents, flow-control agents, antiskinning agents, antifoaming agents, flatting agents, substances for regulating viscosity, catalysts for the NCO—OH/NH reaction and/or for opening the iminooxadiazinedione ring, pigments, dyes, UV absorbers and thermal and oxidative stabilizers.

Coating compositions containing the polycyclic iminooxadiazine-diones according to the invention can be used for the coating of various substrates such wood, plastics, leather, metal, paper, concrete, masonry, ceramics and textiles.

In the following examples, all parts and percentages are by weight, unless otherwise indicated.

EXAMPLES

Example 1

Comparison Example (see also EP-A 571,038, Examples 1–3, and EP-A 57,653 or U.S. Pat. No. 4,412,073)

In each case, 200 g (1.43 moles) of 1,4-diisocyanatobutane (BDI) were placed, at 60° C. (a–c) and 120° C. (d), with stirring, in a 250 ml four-necked flask equipped with mechanical stirrer, internal thermometer, reflux condenser and metering device for the catalyst. The following were then added incrementally, in the total amounts set forth below, over a period of 2–3 hours with external heating or cooling in order to maintain the reaction temperature at 60° C. to 70° C. (a–c) and 120° C. (d):

a) 25 mg of benzyltrimethylammonium hydroxide (Triton B, Aldrich), dissolved in 2-ethyl-1,3-hexanediol, b) 55 mg of N,N', N''-tris(dimethylaminopropyl) hexahydrotriazine (Polycat 41, Air Products), dissolved in n-hexane, c) 8 g of 1,4-diaza[2.2.2]bicyclooctane (DABCO, Air Products), dissolved in butanol, and d) 3 g of bis(trimethylsilyl)amine (HMDS, Aldrich), undiluted.

After the reaction solution had attained a titrimetrically (DIN 53 185) determined NCO content of approx. 53%, the reaction was terminated by the addition in each case of the stoichiometric quantity, corresponding to the quantity of catalyst used, of di-n-butyl phosphate in a)–c) and $H_2O$ in d). The reaction mixtures were then analyzed by means of gel permeation chromatography (GPC). The results are set forth in Table 1.

| Experiment | Proportion of polymer (>2500 g/mol)[1] [area-%][2] | Oligomeric isocyanurate-polyisocyanate[1] [area-%][2] | Other[1] [area-%][2] | D [area-%][2] |
|---|---|---|---|---|
| 1a) | approx. 60 | approx. 18 | approx. 22 | n.d. |
| 1b) | approx. 13 | approx. 82 | approx. 5 | n.d. |
| 1c) | approx. 29 | approx. 55 | approx. 15 | 0.8 |
| 1d) | n.d. | approx. 90 | approx. 9 | 0.6 |

[1]The molecular weight distribution of the polymeric proportions varies a little in the experiments, the average was in most cases above 10,000 g/mol; no investigations into the structure of these polymers were carried out (cf. also Y. Iwakura, K. Uno and K. Ichikawa, Journal of Polymer Science: Part A, 2, (1964) 3387–3404); in addition to isocyanurate polyisocyanates, compounds primarily containing uretdione groups, as well as reaction products of the catalysts or the catalyst solvents (summarized under 'Other') were present.

-continued

| Experiment | Proportion of polymer (>2500 g/mol)[1] [area-%][2] | Oligomeric isocyanurate-polyisocyanate[1] [area-%][2] | Other[1] [area-%][2] | D [area-%][2] |
|---|---|---|---|---|

[2] area-% = area percentage according to GPC without monomer (not standardized); since except for D all species were obtained in the form of a more or less distinct series of oligomers partially overlapping with one another, more precise data was not possible.
n.d. not detectable Since a separation of excess monomer by thin film distillation was possible only in the case of d)(high amounts of polymers in the case of a)–c), cf. Table 1), the virtually polymer-free resins in the three first-named experiments were obtained by extraction, using the procedure described in EP-A 0,571,038, and were reanalyzed after the separating the extracting agent and the coextracted monomer by thin film distillation. The NCO contents were between 27.3% and 29.2% at dynamic visco-sities of the resins, measured at 23° C., of about 5,000 mPa –s in the case of a)–c), and about 15,000 mPa –s in the case of d). The dominance of the isocyanurate structure was clearly proven by IR spectroscopy and NMR spectroscopy. In none of the cases was D found in a molar proportion of above 5 mole %.

Example 2 (According to the Invention)

The procedure of Example 1 was repeated with the exception that 500 g of BDI was oligomerized with the incremental addition of 1.0 to 1.2 g of tributylphosphine (Hoechst) at:
a) 90° C.
b) 60° C.
c) 60° C.
d) 30° C.

The reaction was terminated when the mixture had attained a titrimetrically determined NCO content of:
a) 47.9%
b) 47.9%
c) 21.0% and
d) 43.5%
by the addition of:
a) 0.75 g of methyl p-toluenesulphonate (TSE) and subsequent heating for one hour at 80° C.,
b)–d) in each case 0.06 g of elemental sulphur.

Following thin film distillation of the first two batches at 100° C./0.2 mbar, 173 g of virtually colorless resin were obtained in each case, which had an NCO content of a): 21.6% and b): 18.9% and a viscosity of a): 600 mPa –s and b) 1960 mPa –s (23° C.). The content of monomeric BDI in a) and b) was 0.2% (GPC analysis), in c) it was approx. 10% (GPC analysis) and in d) it was approx. 42% (GPC analysis).

The content (determined by GPC) of bicyclic iminooxadiazinedione D in the oligomeric products (i.e., excluding the monomer present in proportion in c) and d)) is:
a) approx. 36 area-%,
b) approx. 49 area-%,
c) approx. 39 area-%,
d) approx. 48 area-%.

The identity of D is confirmed from the data of the elemental analysis (for the characterization of the substance, cf. also Example 4), from GPC, GC-MS, [1]-H spectroscopy, 13C-NMR spectroscopy and IR spectroscopy. The molar proportion (determined by NMR-spectroscopy) of the iminooxadiazinedione groups, based on the NCO derivatives of the resin, is:
a) approx. 43 mole %,
b) approx. 59 mole %,
c) approx. 69 mole % and
d) approx. 75 mole %.

Example 3 (According to the Invention)

173 g of the resin from Example 2a) was subjected to thin film distillation with a heating medium at a temperature of 180° C. and at a pressure of 0.2 mbar. 134 g of a colorless liquid was distilled off, which was again subjected to a thin film distillation at 120° C./0.2 mbar in order to separate off the monomeric BDI formed at the high distillation temperature from the thermal splitting of uretdione groups. 69 g of a monomer-free product having an NCO content of 22.3% and a dynamic viscosity of 640 mPa –s (23° C.) was obtained. This product contained substantially pure D corresponding to formula (IV) in addition to approx. 60% uretdione E corresponding to formula (V).

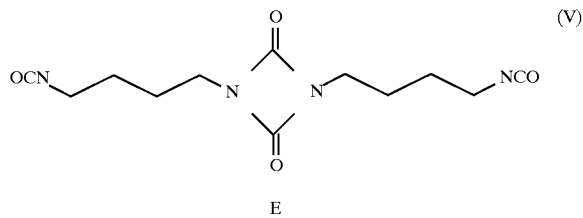

E

Example 4 (According to the Invention)

The procedure of Example 1 was repeated with the exception that 100 g of BDI, dissolved in 900 g of toluene, were placed in the reaction flask and 6 g of tributylphosphine were incrementally added to this mixture. The reaction was conducted at 60° C. until the NCO content of the mixture, determined titrimetrically, was 4.21%. The reaction was terminated by the addition of 1 g of elemental sulphur and then most of the toluene was withdrawn on a rotary evaporator at 50° C./5 mbar. 114.8 g of a liquid having an NCO content of 33.8% was obtained. The NMR spectroscopic analysis of the product proved that approx. 85 mole % of the NCO derivative possesses the bicyclic iminooxadiazinedione structure according to the invention. After the unreacted monomer was removed by distillation, a methylamine solution in toluene, in the stoichiometric quantity corresponding to the titrated NCO equivalent quantity, was added dropwise at room temperature. After complete reaction of the NCO groups as determined by IR, the mixture was slowly concentrated to small volume. At the onset of crystallization the concentration process was discontinued, the crystals were stored in a refrigerator overnight and then the deposited precipitate was filtered under suction, washed several times with cold ether and dried. The elemental analysis of the monomethylurea from D yields the following result: found (calculated for $C_{13}H_{21}N_5O_4$): C: 50.21% (50.15%), H: 6.92% (6.80%),N: 22.48% (22.49%).

Example 5 (according to the Invention, to demonstrate the Heat Stability of the Polycyclic Iminooxadiazinediones)

10 g of a mixture of polyisocyanates, obtained by the procedure described in Example 3 (molar ratio of iminooxadiazinedione to uretdione=0.7), was heated from 150° C. to 180° C., at a pressure which was slowly decreased from 2 to 0.1 mbar, in the course of 50 minutes in a standard distillation apparatus under a fine pearl-like stream of nitrogen passed over by means of a lateral capillary which was not too fine. More than 95% of the distillate passed over (5.0 g) was found from gas-chromatographic analysis to be BDI ($n_D^{20}$=1.4518). The distillation residue was then subjected to a Kugelrohr distillation at 200° C. to 250° C./0.5 mbar. 3.33 g of a colorless liquid was obtained. The NMR spectroscopic analysis showed that the molar ratio of iminooxadiazinedione to uretdione had risen to 2.6.

This experiment proves that the BDI dimer D having a bicyclic iminooxadiazinedione structure, in contrast to the isomeric uretdione dimer E, displayed no detectable tendency to thermally decompose into the original isocyanate (BDI). Therefore, the iminooxadiazinediones according to the invention are extremely resistant to thermal decomposition.

Example 6 (according to the Invention, Model Cross-Linking Reactions in Accordance With Scheme 1)

In each case, to 15 g of the mixture of polyisocyanates from Example 2b) were added, with stirring:

a) 5 g of n-butanol, b) 5 g of n-butanol and 50 mg dibutyltin dilaurate, c) 10 g of n-butanol and d) 10 g of n-butanol and 50 mg dibutyltin dilaurate After the evolution of heat had abated, a) and b) were maintained for two hours at 50° C. and c) and d) were maintained under mild reflux conditions at a bath temperature of 130° C. The mixtures were then analyzed. In a), both unreacted NCO and free butanol were detected. In the IR spectrum of b), the NCO bands were totally absent; the alcohol was completely reacted in the form of urethane. In both a) and b) the molar ratio of iminooxadiazinedione groups to uretdione groups was virtually unaltered from the initial value.

In c) and d) no NCO bands appeared in the IR spectrum. The iminooxadiazinedione ring was only detected by NMR spectroscopy in the case of c). In both c) and d) uretdione groups were clearly detected. Also, the compounds formed from the ring-opening reaction according to Scheme 1 were detected.

Example 7 (According to the Invention, Example of Two-Component Processing Method)

10 g of a mixture of polyisocyanates, obtained by the procedure described in Example 2a), were mixed with 11.1 g of an OH-functional polyester prepared from phthalic anhydride and trimethylolpropane, and having an OH number of 260 (equivalent weight: 215) in 15 g of n-butyl acetate (NCO:OH equivalent ratio=1.1). The coating composition was applied to a glass plate in a layer of 180 μm in thickness and then subjected to forced drying for 30 minutes at 80° C. After 100 MEK double rubs the coating was detached from the substrate.

When a 50% excess of the OH-functional polyester component was used, which would result in a distinct deterioration in the coating properties of the coating obtained if traditional isocyanate curing agents were employed, and when the cross-linking reaction was carried out for 60 minutes at 130° C., a clear coating was obtained, which showed no signs of being detached from the substrate even after 150 MEK double rubs. The improved solvent resistance is a result of additional cross-linking, which commenced at a higher elevated temperature due to the opening of the iminooxadiazinedione rings (cf. Scheme 1).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polycyclic iminooxadiazinedione corresponding to formula (I)

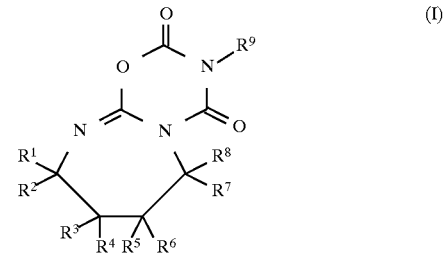

wherein $R^1$ to $R^8$ are identical or different and represent hydrogen or alkyl, cycloalkyl, aralkyl and aryl groups, which may be substituted by isocyanato(cyclo)alkyl groups or by groups which are not reactive with isocyanate groups, or $R^1$ and/or $R^2$ form one or more, optionally partially unsaturated rings, with one another and also with one or more substituents from among $R^3$ to $R^8$ and the corresponding carbon atoms of the seven membered ring segment in A or $R^3$ or $R^4$ form an aromatic ring with $R^5$ or $R^6$ and with the two carbon atoms of the seven-membered ring segment in A which are not bonded to nitrogen, and $R^9$ represents hydrogen or an alkyl, cycloalkyl, alralkyl, aryl, or heterocyclic, group which may be substituted by isocyanato(cyclo)alkyl groups or by groups which are not reactive with isocyanate groups.

2. The polycyclic iminooxadiazinedione of claim 1, wherein $R^9$ represents a group corresponding to formula II

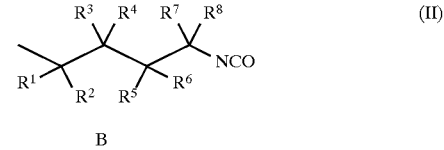

wherein $R^1$ to $R^8$ are as previously defined.

3. The polycyclic iminooxadiazinedione of claim 1 which has been prepared from an optionally branched, open-chain aliphatic diisocyanate wherein the two isocyanate groups are arranged in the 1,4 positions to one another.

4. 10-(4-isocyanatobutyl)-8-oxa-1,6,10-triazabicyclo-undec-6-en-9,11-dione corresponding to the formula

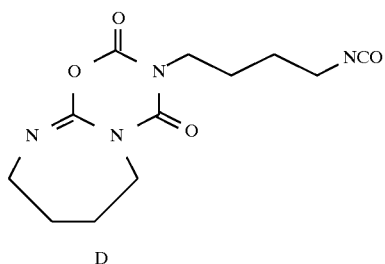 (IV)

5. A composition containing at least 10 mole % of the polycyclic iminooxadiazinedione of claim 1, in which the remainder comprises an isocyanate derivative containing isocyanurate, uretdione, biuret, allophanate, carbodiimide and/or urethane groups wherein the isocyanate groups may optionally be present in blocked form.

6. A composition for the preparation of an optionally foamed, polyurethane plastics or for the production of a coating which contains the polycyclic iminooxadiazinedione of claim 1.

* * * * *